United States Patent

Bonnet

[11] Patent Number: 5,307,804
[45] Date of Patent: May 3, 1994

[54] ENDOSCOPE HAVING A CAMERA COUPLED THERETO

[75] Inventor: Ludwig Bonnet, Knittlingen, Fed. Rep. of Germany

[73] Assignee: Richard Wolf GmbH, Knittlingen, Fed. Rep. of Germany

[21] Appl. No.: 825,210

[22] Filed: Jan. 24, 1992

[30] Foreign Application Priority Data

Feb. 21, 1991 [DE] Fed. Rep. of Germany ....... 4105326

[51] Int. Cl.$^5$ .............................................. A61B 1/06
[52] U.S. Cl. ......................................... 126/7; 126/4; 354/62
[58] Field of Search .................... 126/4, 7; 124/89; 354/62, 286

[56] References Cited

U.S. PATENT DOCUMENTS

| | | | |
|---|---|---|---|
| 3,589,350 | 6/1971 | Hovt, Jr. | 124/89 |
| 4,248,213 | 3/1981 | Landre . | |
| 4,781,448 | 11/1988 | Chatenever et al. . | |
| 4,844,071 | 7/1989 | Chen et al. | 128/4 X |
| 4,851,866 | 7/1989 | Ciarlei et al. . | |

FOREIGN PATENT DOCUMENTS

| | | |
|---|---|---|
| 0058020 | 8/1982 | European Pat. Off. . |
| 1840515 | 9/1961 | Fed. Rep. of Germany . |
| 2757358 | 6/1978 | Fed. Rep. of Germany . |
| 7918414 | 10/1979 | Fed. Rep. of Germany . |
| 3429945 | 4/1985 | Fed. Rep. of Germany . |

*Primary Examiner*—Richard J. Apley
*Assistant Examiner*—Beverly A. Meindl
*Attorney, Agent, or Firm*—Panitch Schwarze Jacobs & Nadel

[57] ABSTRACT

In an endoscope with a camera objective, in particular a video camera objective, coupled to the eyepiece cup of the endoscope at its proximal end, the objective is mounted so that it is free to rotate on the proximal end of the eyepiece cup. The camera objective and its camera head have a center of gravity which is offset from the axis of rotation of the objective so that the objective maintains its orientation if the endoscope is rotated about its longitudinal axis, whereby such rotation of the endoscope does not affect the endoscopic picture displayed on a monitor of the video camera.

9 Claims, 1 Drawing Sheet

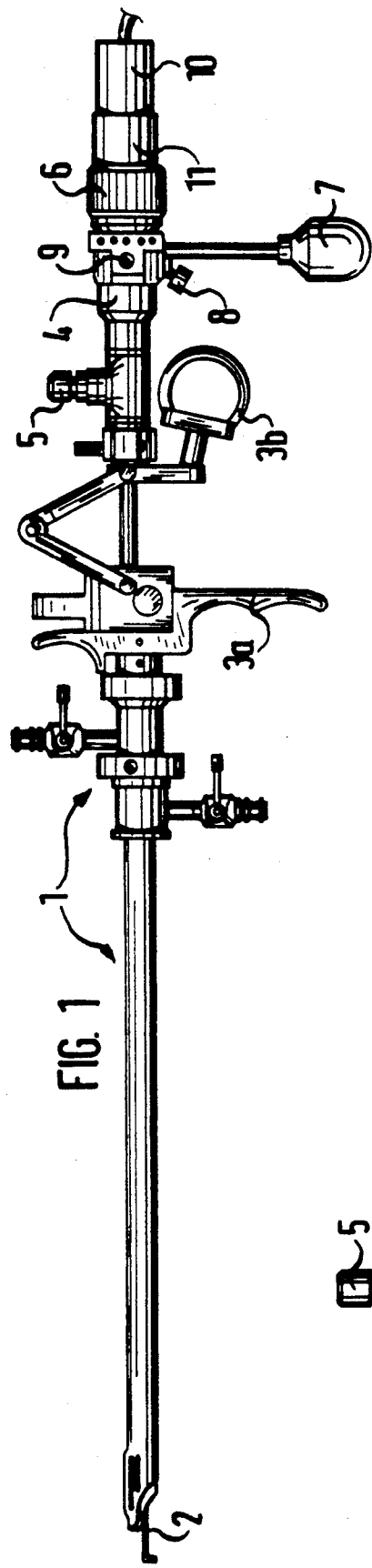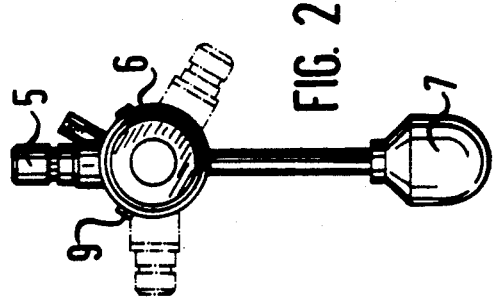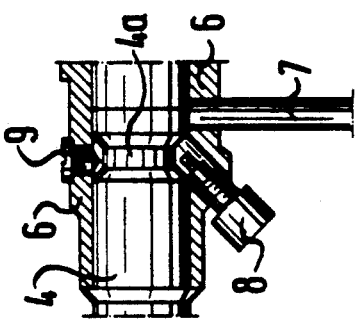

ENDOSCOPE HAVING A CAMERA COUPLED THERETO

FIELD OF THE INVENTION

This invention relates to an endoscope having a camera coupled thereto.

A camera, and especially a video camera for the transmission of images from body cavities and/or for the documentation of diagnostic reports, may be detachably but otherwise rigidly, coupled by the objective of the camera to an eyepiece cup of the endoscope.

BACKGROUND OF THE INVENTION

Connections and quick-release couplings for the above purpose are disclosed in DE-U 1840515, DE-U 7918414, DE-A- 3429945 and DE-B 2757358. These specifications teach the use of a fixed connection between the eyepiece cup and the camera, which prevents the camera from rotating on the eyepiece cup. In many cases this makes the entire unit which consists of the endoscope and/or the lens unit thereof, the objective with quick-release coupling, and the camera awkward to handle, especially in circumstances where the point of access of the endoscope when in use, to a chosen area of tissue, needs to be varied, whilst the viewing position of the camera remains unchanged; for example for staunching bleeding, effecting coagulation or making an incision.

Although in principle the endoscope, when in use, may be rotated about its longitudinal axis to only a slight or to a restricted extent, such as when a coagulating-cutting loop is used for example, rigid attachment of the camera to the eyepiece cup of the endoscope lens unit, has the disadvantage that the image is simultaneously rotated, so that an endoscopic picture displayed by means of a monitor may cause the observer to become disorientated.

In order to correct such image reorientation the operating surgeon must interrupt the operation thereby increasing its duration and also, disturbing his concentration.

SUMMARY OF THE INVENTION

An object of the invention is to avoid these disadvantages by so constructing the coupling between camera objective and endoscope that any rotation of the image is automatically compensated for, and thus prevented, without the use of electronic measuring and positioning devices.

According to the present invention, in an endoscope with the objective of a camera, in particular a video camera, releasably coupled to the proximal end of the endoscope, the objective is mounted so as to be capable of rotating freely on the endoscope and the center of gravity of the camera components connected to the endoscope being offset with respect to the axis of rotation so that the camera objective maintains its orientation by pendulum action if the endoscope is rotated.

BRIEF DESCRIPTION OF THE DRAWINGS

FIG. 1 is an elevational view of a resectoscope according to an embodiment of the present invention, to which the mounting of an objective of a video camera is coupled;

FIG. 2 is a partial proximal end view of the objective; and

FIG. 3 is an enlarged longitudinal section through the said objective and neighbouring parts of the endoscope.

DETAILED DESCRIPTION OF THE INVENTION

An endoscope in the form of a resectoscope 1, has a shaft provided at the open, distal end thereof with an HF cutting loop 2 which is axially displaceable by means of a handle 3a,3b for making a longitudinal section, for example to remove prostate tissue. Located at the proximal end of the working section of the resectoscope 1, which section is detachably coupled to an outer shaft of the resectoscope is the eyepiece cup 4 of an endoscope lens unit 5. The cup 4 is releasably mounted in said working section, the distal end of the objective 6, comprising a mounting and a lens of a video camera being rotatably secured to the cup 4 by means of ball catch elements 9 and being secured against unintentional release by means of a screw 8 engaging in an annular groove 4a in the eyepiece cup 4. Apart from the objective 6, only the camera head 10 of the video camera is shown. The screw 8 can be screwed into the mounting of the objective 6 of the video camera, which mounting is provided with a stop shoulder to prevent the screw 8 from coming into contact with the bottom of the annular groove 4a and thus preventing rotation of the objective 6 on the eyepiece cup 4. The camera head 10 is screwed into the proximal end 11 of the mounting part of the objective 6.

The center of gravity of the objective 6 which is rotatably mounted on the eyepiece cup 4 as aforesaid, is offset from the axis of rotation of objective 6. In this embodiment such offset is achieved by rigidly connecting a downwardly directed pendulum weight 7 to the objective 6. If need be another pendulum of a different weight may be substituted for the pendulum weight 7. In either case the position of the objective 6 and/or the shooting position of the video camera is maintained should the endoscope 1 need to be rotated, for example to act upon a particular area of tissue, this being by virtue of the pendulum mounting of the camera, or camera head, on the endoscope. Thus rotation of the endoscope about its longitudinal axis cannot affect the endoscopic picture displayed by the camera on a visual monitor (not shown); that is to say, rotational movement of the objective 6 together with the rotation of the endoscope is prevented or is largely restrained, by the action of the pendulum weight 7.

The upper end of the pendulum weight 7 may engage in the annular groove 4a in the eyepiece cup 4, thereby securing the connection of the freely rotatable objective 6 to the eyepiece cup 4, and enabling the screw 8 to be omitted.

The center of the center of gravity of the camera or the objective can also be offset for the purpose described above by replacing the single pendulum 7 by two downwardly angled diverging stabilizers (not shown) laterally located directly on the mounting part of the objective.

No separate pendulum need be provided if the center of gravity of the camera components connected to the endoscope can be offset in relation to the axis of rotation whereby this alone keeps the camera objective suspended in the same position independently of any rotation of the endoscope about its longitudinal axis.

What is claimed is:

1. An endoscope having a longitudinal axis and a proximal end with an objective of a camera releasably coupled thereto, wherein the objective is coupled to said proximal end so as to be capable of free rotation thereon about an axis of rotation, the center of gravity of those camera components which are connected to the endoscope being offset with respect to said axis of rotation such that gravity exclusively maintains the angular orientation of the objective by pendulum action when the endoscope is rotated about said longitudinal axis, the endoscope having a downwardly directed pendulum connected to said objective for offsetting said center of gravity.

2. An endoscope having a longitudinal axis and a proximal end with an objective of a camera releasably coupled thereto, wherein the objective is coupled to said proximal end so as to be capable of free rotation thereon about an axis of rotation, the center of gravity of those camera components which are connected to the endoscope being offset with respect to said axis of rotation such that gravity exclusively maintains the angular orientation of the objective by pendulum action when the endoscope is rotated about said longitudinal axis, the endoscope having two downwardly angled stabilizers located on a mounting of the objective for offsetting said center of gravity.

3. An endoscope having a longitudinal axis and a proximal end with an objective of a camera releasably coupled thereto, wherein the objective is coupled to said proximal end so as to be capable of free rotation thereon about an axis of rotation, the center of gravity of those camera components which are connected to the endoscope being offset with respect to said axis of rotation such that gravity exclusively maintains the angular orientation of the objective by pendulum action when the endoscope is rotated about said longitudinal axis, the endoscope having an eyepiece cup provided with an annular grove, a mounting of the objective having a ball catch engaging in said groove.

4. An endoscope having a longitudinal axis and a proximal end with an objective of a camera releasably coupled thereto, wherein the objective is coupled to said proximal end so as to be capable of free rotation thereon about an axis of rotation, the center of gravity of those camera components which are connected to the endoscope being offset with respect to said axis of rotation such that gravity exclusively maintains the angular orientation of the objective by pendulum action when the endoscope is rotated about said longitudinal axis, the endoscope having an eyepiece cup provided with an annular groove, a screw mounted in a mounting of the objective engaging in the annular groove.

5. An endoscope as claimed in claim 1, wherein the endoscope has an eyepiece cup provided with an annular groove, the pendulum engaging in said annular groove.

6. An endoscope as claimed in claim 1, wherein said camera is a video camera.

7. An endoscope as claimed in claim 2, wherein said camera is a video camera.

8. An endoscope as claimed in claim 3, wherein said camera is a video camera.

9. An endoscope as claimed in claim 4, wherein said camera is a video camera.

* * * * *